United States Patent
Castellani et al.

(10) Patent No.: US 8,728,740 B2
(45) Date of Patent: May 20, 2014

(54) MONOCLONAL ANTIBODY AND ITS USE FOR THE IDENTIFICATION OF THE ONCOFETAL ISOFORM OF FIBRONECTIN (B-FN) FOR DIAGNOSIS OR THERAPY

(75) Inventors: Patrizia Castellani, Genoa (IT); Francesca Sassi, Trofarello (IT); M. Barbara Carnemolla, Genoa (IT); Laura Borsi, Genoa (IT); Enrica Balza, Genoa (IT)

(73) Assignee: Sirius-Biotech S.R.L., Genoa (IT)

( * ) Notice: Subject to any disclaimer, the term of this patent is extended or adjusted under 35 U.S.C. 154(b) by 72 days.

(21) Appl. No.: 13/139,112

(22) PCT Filed: Dec. 11, 2009

(86) PCT No.: PCT/EP2009/066907
§ 371 (c)(1),
(2), (4) Date: Jul. 11, 2011

(87) PCT Pub. No.: WO2010/066872
PCT Pub. Date: Jun. 17, 2010

(65) Prior Publication Data
US 2011/0256060 A1    Oct. 20, 2011

(30) Foreign Application Priority Data
Dec. 12, 2008  (IT) .......................... FI2008A000240

(51) Int. Cl.
*G01N 33/53*     (2006.01)

(52) U.S. Cl.
USPC ............ 435/7.1; 435/332; 435/334; 435/337; 530/350; 530/387.1; 530/387.3; 530/388.22; 530/388.25; 530/391.3; 530/391.7

(58) Field of Classification Search
USPC .......... 530/350, 387.1, 387.3, 388.2, 388.22, 530/388.25, 391.3, 391.7; 435/332, 334, 435/337, 7.1
See application file for complete search history.

(56) References Cited

PUBLICATIONS

Schwarzbauer (Bioessays. Oct. 1991;13 (10): 527-33).*
Peters et al. (J. Lab. Clin. Med. Jun. 2003; 141 (6): 401-10).*
Campbell (Monoclonal Antibody Technology, Laboratory Techniques in Biochemistry and Molecular Biology, 1984, Elsevier Science Publishers B.V.: Amsterdam, The Netherlands, vol. 13, pp. 1-32).*

* cited by examiner

*Primary Examiner* — Stephen Rawlings
(74) *Attorney, Agent, or Firm* — Abelman, Frayne & Schwab

(57) ABSTRACT

Epitopes localized on FNIII-8 repeat that are normally cryptic but are unmasked by insertion of FNIII-B into the FN molecule and are recognized by specific ligands are described; antibodies or their fragments able to identify the above said epitope are also described.

9 Claims, 7 Drawing Sheets

Sequences of the variable regions of the mAb C6.

Sequence VH :    (SEQ ID NO: 5)

5'
AAGGTGCAGCTGCAGGAGTCAGGTGGAGGATTGGTGCAGCCTAAAGGGT
CATTGAAAATCTCATGTGCAGCCTCTGGACTCACCTTCAACAGCTACGCCA
TGAACTGGGTCCGCCAGGCTCCAAGAAAGGGTTTGGAATGGGTTGCTCGC
ATAAGAAGTAAAAGTAATAATTATGCAACATATTATGCCGATTCAGTGAA
AGACAGGTTCACCATCTCCAGAGATGATTCACAAAGCATGCTCTATCTGC
AAATGAACAACTTGAAAACTGAGGACACAGCCATGTATTACTGTGTGAAA
CAGGGGGGTAACTCCCTTTACTGGTACTTCGATGTCTGGGGCGCAGGGAC
CACGGTCACCGTCTCCTCAGCCAAAACGACACCCCCATCTGTCTATCCAC
TGGCCAA 3'

Sequence Vk :    (SEQ ID NO: 6)

5'
GATATTGTGATGAGCCAGTCTCCATCCTCCCTAGCTGTGTCAGTTGGAGAG
AAGGTTACTATGAGCTGCAAGTCCAGTCAGAGCCTTTTATATAGTAGCAA
TCAAAAGAACTACTTGGCCTGGTACCAGCAGAGACCAGGGCAGTCTCCTA
AACTGCTGATTTACTGGGCATCCACTGGGGAATCTGGGGTCCCTGATCGCT
TCACAGGCAGTGGATCTGGGACAGATTTCACTCTCACCATCAGCAGTGTG
AAGGCTGAAGACCTGGCAGTTTATTACTGTCAGCAATATTATAGCTATCC
GCTCACGTTCGGTGCTGGGACCAAGCTGGAGCTGAAACGGGCTGATGCTG
CACCAACTGTATCCAAA 3'

Figure 5

MONOCLONAL ANTIBODY AND ITS USE FOR THE IDENTIFICATION OF THE ONCOFETAL ISOFORM OF FIBRONECTIN (B-FN) FOR DIAGNOSIS OR THERAPY

RELATED APPLICATIONS

This application is a §371 of PCT/EP2009/066907 filed Dec. 11, 2009, and claims priority from Italian Patent Application No. FI2008A000240 filed Dec. 12, 2008, both incorporated by reference in their entirety.

FIELD OF INVENTION

The present invention is referred to the field of diagnostics, in particular those that are capable of highly specific identifications through murine monoclonal antibodies and their conjugates.

STATE OF ART

Fibronectins (FNs) are adhesive and polymorphic glycoproteins present in biological fluids and extracellular matrices. These molecules are involved in several biological processes, such as cellular morphology, cellular migration, wound healing, angiogenic processes and neoplastic transformation. FN polymorphism is at least partially due to alternative splicing in three regions (IIICS, ED-A and FNIII-B) of the pre m-RNA coded for by a single gene. In all processes of tissue remodeling, both physiological (embryogenesis, wound healing, proliferative phase of endometrium) or pathological (for example, neoplasia), the pre-mRNA splicing pattern of FN is altered and generates an augmented expression of the isoforms containing the FNIII-B domain. In particular, the FN isoforms containing the FNIII-B domain (BFNs) are, with very rare exceptions, undetectable in normal adult tissues but show a considerable expression in fetal tissues, neoplastic tissues and tissues undergoing wound healing. Moreover, the accumulation of BFN around newly formed blood vessels makes it an important angiogenic marker (Carnemolla et al. 1989; Castellani et al. 1994; Castellani et al. 2002).

Studies thus far have identified a single epitope localized within the type III repeat 7 (FNIII-7) that, while cryptic in FN molecules lacking the FNIII-B domain, is unmasked when FNIII-B is inserted into the molecule and can interact with specific ligands for BFN, i.e., antibodies, the prototype of which is the mouse monoclonal antibody (mab) BC-1.

The mab BC-1, specific for human BFN (Carnemolla et al. 1989), has been extensively used to study the distribution of BFN in angiogenic processes, in neoplasms and in different types of pathologies. This mab recognizes the epitope described above.

On the basis of the studies carried out with the murine mab BC-1, it was demonstrated that BFN may be a very good target for malignancies and for all angiogenesis-associated pathologies. In light of the above, the need is clear for mabs that can recognize new epitopes detectable only in the oncofetal BFN isoform, and that can be generated in substantial quantities and always on highly specific epitopes and thereafter utilized as an additional means for novel therapeutics or diagnostics.

BRIEF DESCRIPTION OF FIGURES

FIG. 5: cDNA coding sequences of the variable regions VET and VLk of C6 mab (SEQ ID NOS: 5 and 6, respectively).

DETAILED DESCRIPTION OF THE INVENTION

The repeat FNIII-8 (FIG. 1) contains an epitope, which, while normally cryptic, is unmasked by insertion in the FN molecule of the repeat FNIII-B, thereby making it accessible to specific ligands and enabling the identification of the oncofetal BFN isoform.

In particular, the invention refers to an epitope, hereinafter named C6, and to the murine monoclonal antibody (hereinafter named C6 mab), which is able to specifically recognize the above-mentioned epitope and hence the oncofetal BFN isoform. The invention also refers to all conjugates and derivatives formed by the said antibody and drugs or molecules able to act as diagnostic (e.g., radioactive isotopes, fluorescent substances, etc.) or therapeutic agents (e.g., radioactive isotopes, cytokines, chemotherapeutics, etc.) for neoplasms and other pathologies where BFN is expressed, the conjugation of the mab C6, subject of the invention, and the aforementioned agents being achieved following procedures normally used in this field for the preparation of similar products.

Experimental Description

Generation and characterization of the mab C6 and identification of a new epitope in the FNIII-8 repeat, cryptic in FN molecules lacking FNIII-B but available to the antibody when FNIII-B is inserted in the FN molecules.

FN was purified from human plasma and from the conditioned medium of WI38-VA13 cells according to Zardi et al. (1980).

FN recombinant fragments were produced and purified according to Carnemolla et al. (1992).

Murine hybridoma was generated by fusing splenocytes from immunized mice with murine myeloma SP2/0Ag14 cells, following a procedure described by Zardi et al. (1980).

ELISA was performed according to Carnemolla et al. (1996).

Immunohistochemistry on cryosections was performed according to Castellani et al. (2002).

SDS-PAGE and Western Blotting were carried out according to Zardi et al. (1987).

In order to sequence the variable regions of mab C6, total RNA was purified from C6 hybridoma cells and used as template to amplify the cDNA of the VH and VL by RT-PCR with the following primers: 5' gatattgtgatgacccagtctccca 3' (VL forward) (SEQ ID NO: 1); 5' tggatacagttggtgcagc 3' (VL, reverse) (SEQ ID NO: 2); 5' aggtg(c)c(a)ctgcagg(c)agtct(a)gg 3' (VH, forward) (SEQ ID NO: 3); 5' ggccagtggatagac 3' (VH, reverse) (SEQ ID NO: 4). The resulting amplification products were sequenced.

Female Balb/C mice, aged 5-6 weeks, were immunized following the protocol described by Zardi et al. (1980) using the FNIII-7B89 recombinant fragment (FIGS. 1-2).

Figure 1:
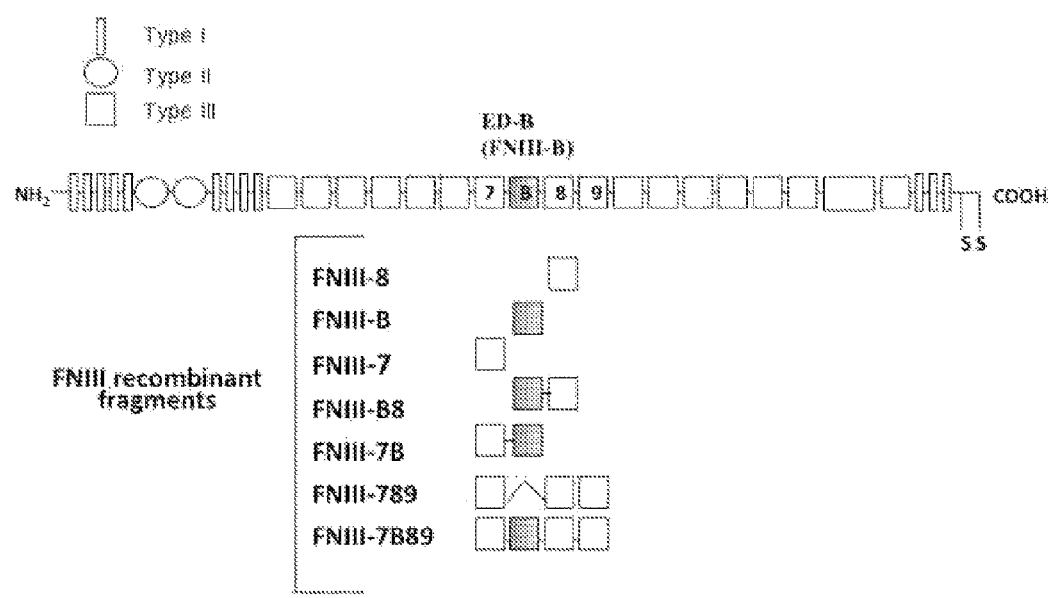
FIG. 1 shows a model of the domain structure of a human FN subunit and indicates the three types of homology repeats (I, II, III) that constitute FN and the structure of the recombinant fragments of FN.
Figure 2:
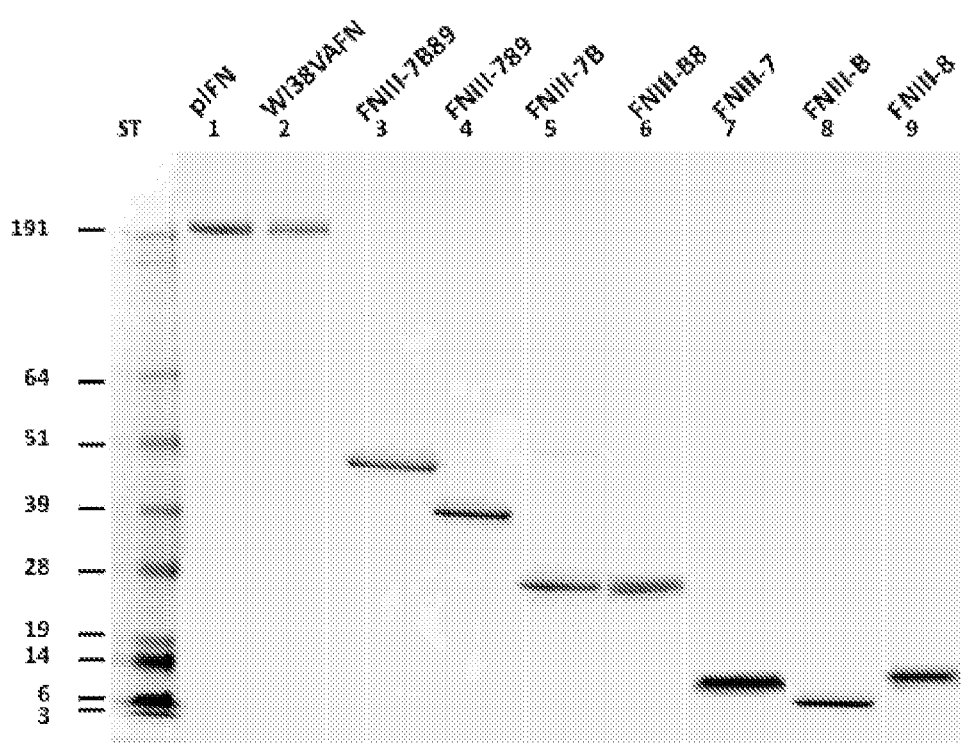
FIG. 2 shows the results of SDS-PAGE analysis of plasma FN (pIFN, lane 1), FN derived from tumoral cell line WI38-VA13 (WI38VAFN; lane 2) and the different recombinant FN fragments (lanes 3-9); the numbers on the left are the molecular mass of the standards (ST).

The hybridoma clones obtained by fusing the splenocytes of the immunized mice and myeloma SP2/0Ag14 cells were tested by ELISA for reactivity with FNIII-7B89 and FNIII-789 fragments (FIGS. 1-2).

Clone C6 mab was chosen from among the clones that produced antibodies positive for FNIII-7B89 and negative for FNIII-789 and was then expanded for purification and characterization.

Figure 4:
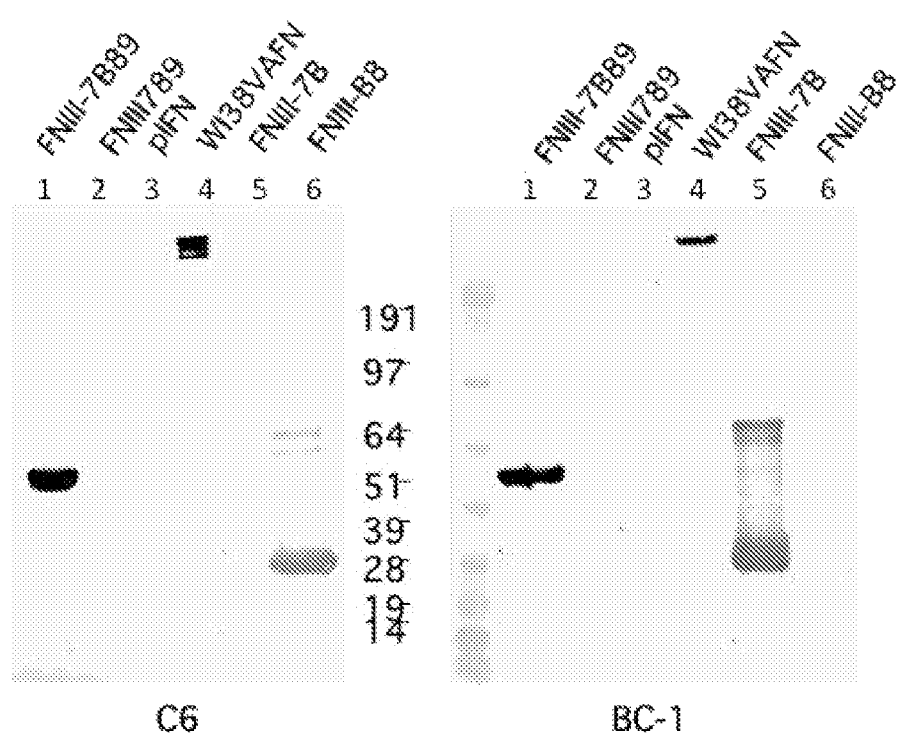
FIG. 4: Results of Western Blot analysis using C6 and BC-1 mabs on FN purified from plasma (pIFN) and from the conditioned medium of SV-40 transformed cells (WI38VAFN) and on the indicated FN fragments.

As reported in FIG. 4, C6 mab had a negative reactivity with FN purified from human plasma (without FNIII-B) and a positive reactivity with FN purified from the conditioned medium of the SV-40 transformed human fibroblasts, WI38-VA13, that release significant amounts of BFN into the culture medium.

Figure 3:
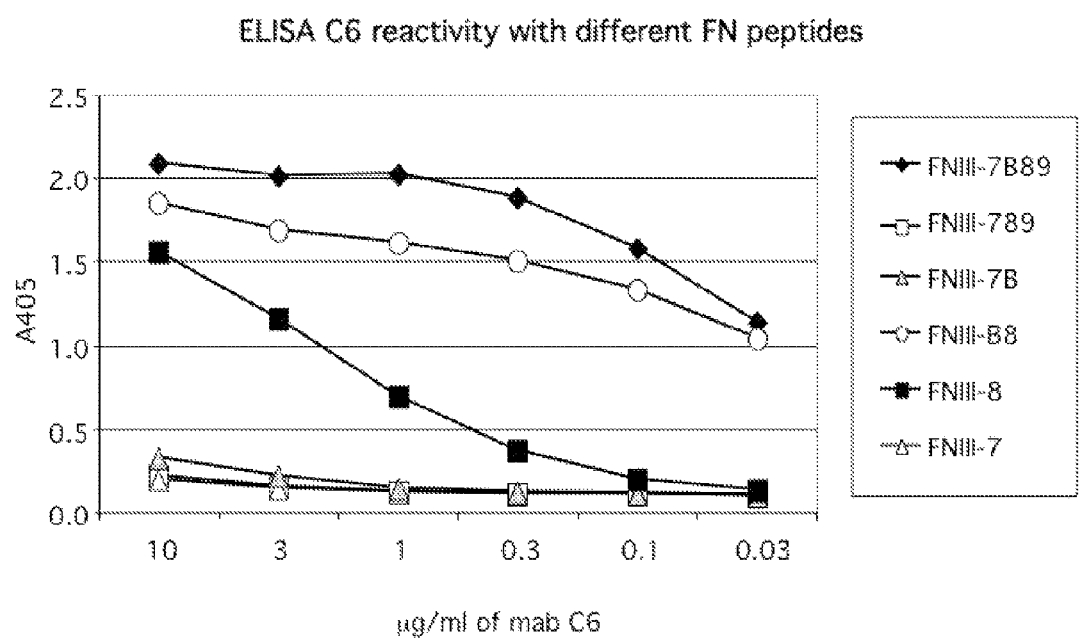
FIG. 3: Reactivity of the purified C6 mab (according to the invention) on ELISA test, with the recombinant FN fragments listed in the insert.

Results of ELISA experiments using purified C6 mab (FIG. 3) indicate that mab C6 does not react directly with FNIII-B domain. In fact, the mab C6 does not react with FNIII-789, but it does with FNIII-7B89; it does not react with FNIII-7B, but it shows positivity with FNIII-B8 and also with FNIII-8 alone. This demonstrates that the epitope is localized in the FNIII-8 repeat. In keeping with the ELISA results reported in FIG. 3, the results of the Western Blot analysis shown in FIG. 4 indicate that while BC-1 mab reacts with the FNIII-7B fragment, C6 mab reacts with FNIII-B8.

In ELISA experiments, C6 mab showed no cross-reactivity with FNIII homology fragments of human TN-C and FN that were tested. The sequences of the cDNAs coding for the variable regions VH and VLk of the mab C6 are reported in FIG. 5 and SEQ ID NOS: 5 and 6.

Immunohistochemical Analysis.

Immunohistochemical experiments on cryosections of human normal and neoplastic tissues were carried out using C6 mab; the results are reported in Table 1.

TABLE 1

Immunohistochemical reactivity of C6 mAb on cryostat sections of human tissues

| | | |
|---|---|---|
| human tumors tested | mesothelioma | positive |
| | melanoma | positive |
| | lung carcinoma | positive |
| | glioblastoma | positive |
| human normal tissues tested | breast | negative |
| | heart | negative |
| | esophagus | negative |
| | muscle | negative |
| | thymus | negative |
| | spleen | negative |
| | thyroid | negative |
| | nerve | negative |
| | brain | negative |
| | testis | negative |
| | liver | negative |
| | lung | negative |
| | parotide | negative |
| | lymph-node | negative |

Figure 6:
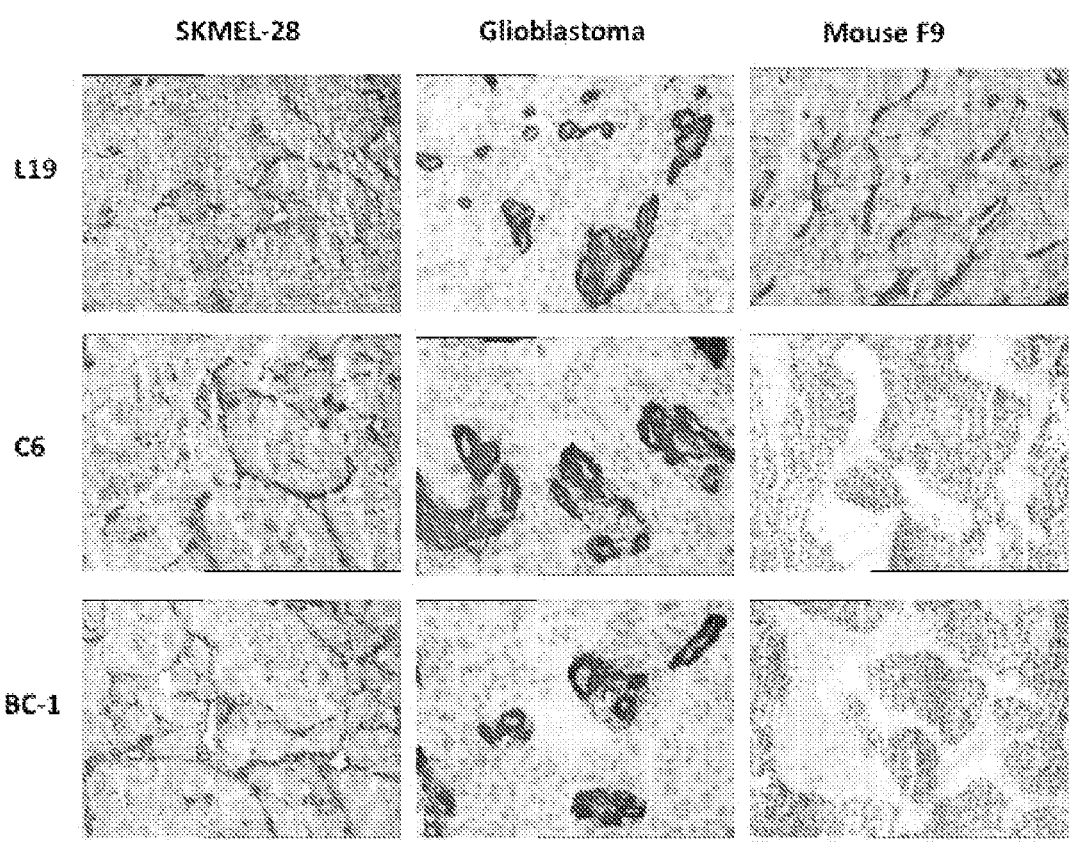
FIG. 6: results of immunohistochemical experiments on cryosections of human and murine neoplastic tissues using the mabs C6 and BC-1 and L19scFv, specific for BFN.

The staining pattern of C6 mab was compared with that of BC-1 mab and L19scFv (specific for FNIII-B) on serial sections of F9 murine teratocarcinoma, and SKMEL-28 human melanoma, both developed in SCID mice, and on sections of a patient derived glioblastoma specimen (FIG. 6). All three antibodies displayed a similar staining pattern on human tumor sections (SKMEL-28 and glioblastoma), while only L19scFv stained the F9 murine tumor sections, as expected, because FNIII-B sequence is identical in mouse and human.

Figure 7:
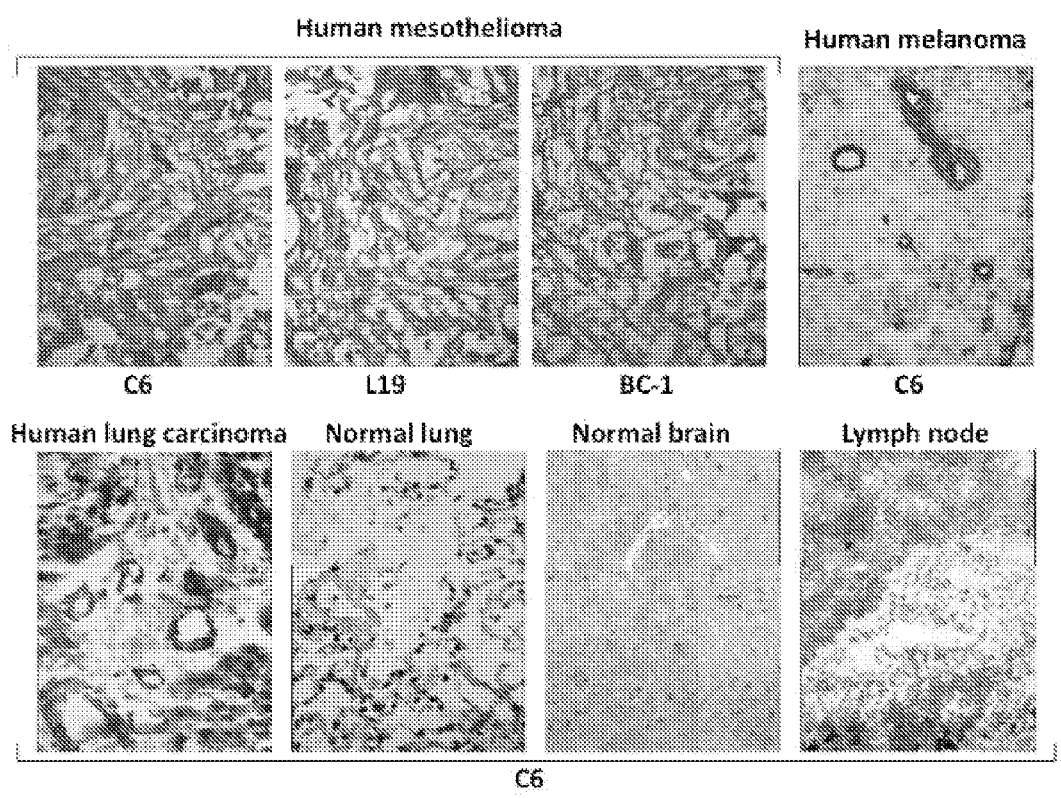
FIG. 7: shows the results of immunohistochemical experiments with the indicated antibodies specific for BFN on serial sections of human mesothelioma, human squamous cell lung carcinoma and human melanoma, and of some normal human tissues (lung, brain and lymph-node).

FIG. 7 reports the concordant results of immunohistochemical experiments conducted with C6 mab, L19scFv and BC-1 mab on serial sections of a patient-derived mesothelioma specimen. Also shown are the results obtained with C6 mab on cryosections of a patient-derived human melanoma and of a squamous cell lung carcinoma specimens and on sections obtained from normal human tissues (lung, brain, lymph node).

As demonstrated by the results reported above, C6 mab is a new tool for both diagnostic and therapeutic approaches to BFN-targeting, as well as for the continued study of the possible biological functions of FN regions unmasked by the insertion of FNIII-B.

The invention claimed is:

1. An isolated antibody which binds specifically to a peptide epitope which consists of an amino acid sequence which is found in a fibronectin III-8 repeat, or a binding fragment thereof, comprising a VH region encoded by SEQ ID NO: 5, and a VLk region encoded by SEQ ID NO: 6.

2. The isolated antibody or binding fragment thereof of claim 1, wherein said antibody is a monoclonal antibody.

3. A hybridoma cell line which produces the monoclonal antibody of claim 2.

4. A conjugate of the isolated antibody or binding fragment of claim 1 and a diagnostic or therapeutically active molecule.

5. The conjugate of claim 4, wherein said diagnostic molecule is a fluorescent molecule or a radioactive isotope.

6. The conjugate of claim 4, wherein said therapeutically active molecule is a radioactive isotope, a cytokine, or a chemotherapeutic agent.

7. A method for determining a fibronectin isoform which contains a fibronectin III-B domain, comprising contacting a sample with the antibody or binding fragment of claim 1, and determining binding as an indication of presence of said fibronectin isoform.

8. The method of claim 7, wherein said sample is a biological fluid.

9. The method of claim 7, wherein said sample is a tissue.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial
<220> FEATURE:
<223> OTHER INFORMATION: PRIMER
<220> FEATURE:
<221> NAME/KEY: primer
<222> LOCATION: (1)..(25)
<220> FEATURE:
<221> NAME/KEY: 5'
<222> LOCATION: (1)..(1)
<220> FEATURE:
<221> NAME/KEY: 3'
<222> LOCATION: (25)..(25)

<400> SEQUENCE: 1
gatattgtga tgacccagtc tccca                                      25
```

-continued

```
<210> SEQ ID NO 2
<211> LENGTH: 19
<212> TYPE: DNA
<213> ORGANISM: Artificial
<220> FEATURE:
<223> OTHER INFORMATION: PRIMER
<220> FEATURE:
<221> NAME/KEY: 5'
<222> LOCATION: (1)..(1)
<220> FEATURE:
<221> NAME/KEY: primer
<222> LOCATION: (1)..(19)
<220> FEATURE:
<221> NAME/KEY: 3'
<222> LOCATION: (19)..(19)

<400> SEQUENCE: 2
tggatacagt tggtgcagc                                                     19

<210> SEQ ID NO 3
<211> LENGTH: 20
<212> TYPE: DNA
<213> ORGANISM: Artificial
<220> FEATURE:
<223> OTHER INFORMATION: primer
<220> FEATURE:
<221> NAME/KEY: 5'
<222> LOCATION: (1)..(1)
<220> FEATURE:
<221> NAME/KEY: primer
<222> LOCATION: (1)..(20)
<220> FEATURE:
<221> NAME/KEY: residue
<222> LOCATION: (5)..(5)
<223> OTHER INFORMATION: in this position the residue is selected from G
      or C
<220> FEATURE:
<221> NAME/KEY: residue
<222> LOCATION: (6)..(6)
<223> OTHER INFORMATION: in this position the residue is selected from C
      or A
<220> FEATURE:
<221> NAME/KEY: residue
<222> LOCATION: (13)..(13)
<223> OTHER INFORMATION: in this position the residue is selected from G
      or C
<220> FEATURE:
<221> NAME/KEY: residue
<222> LOCATION: (18)..(18)
<223> OTHER INFORMATION: in this position the residue is selected from T
      or A
<220> FEATURE:
<221> NAME/KEY: 3'
<222> LOCATION: (20)..(20)

<400> SEQUENCE: 3
aggtsmctgc agsagtcwgg                                                    20

<210> SEQ ID NO 4
<211> LENGTH: 15
<212> TYPE: DNA
<213> ORGANISM: Artificial
<220> FEATURE:
<223> OTHER INFORMATION: primer
<220> FEATURE:
<221> NAME/KEY: 5'
<222> LOCATION: (1)..(1)
<220> FEATURE:
<221> NAME/KEY: primer
<222> LOCATION: (1)..(15)
<220> FEATURE:
<221> NAME/KEY: 3'
<222> LOCATION: (15)..(15)

<400> SEQUENCE: 4
```

```
ggccagtgga tagac                                                            15

<210> SEQ ID NO 5
<211> LENGTH: 407
<212> TYPE: DNA
<213> ORGANISM: Artificial
<220> FEATURE:
<223> OTHER INFORMATION: heavy chain
<220> FEATURE:
<221> NAME/KEY: 5'
<222> LOCATION: (1)..(1)
<220> FEATURE:
<221> NAME/KEY: chainheavy
<222> LOCATION: (1)..(407)
<220> FEATURE:
<221> NAME/KEY: 3'
<222> LOCATION: (407)..(407)

<400> SEQUENCE: 5
aaggtgcagc tgcaggagtc aggtggagga ttggtgcagc taaagggtc attgaaaatc            60 tcatgtgcag cctctggact caccttcaac acctacgcca tgaactgggt ccgccaggct          120
ccaagaaagg gtttggaatg ggttgctcgc ataagaagta aagtaataa ttatgcaaca           180 tattatgccg attcagtgaa agacaggttc accatctcca gagatgattc acaaagcatg          240
ctctatctgc aaatgaacaa cttgaaaact gaggacacag ccatgtatta ctgtgtgaaa          300
caggggggta actcccttta ctggtacttc gatgtctggg gcgcagggac cacggtcacc          360
gtctcctcag ccaaaacgac accccatct gtctatccac tggccaa                         407

<210> SEQ ID NO 6
<211> LENGTH: 369
<212> TYPE: DNA
<213> ORGANISM: Artificial
<220> FEATURE:
<223> OTHER INFORMATION: light chain
<220> FEATURE:
<221> NAME/KEY: 5'
<222> LOCATION: (1)..(1)
<220> FEATURE:
<221> NAME/KEY: chainlight
<222> LOCATION: (1)..(369)
<220> FEATURE:
<221> NAME/KEY: 3'
<222> LOCATION: (369)..(369)

<400> SEQUENCE: 6
gatattgtga tgacccagtc tccatcctcc ctagctgtgt cagttggaga gaaggttact           60
atgagctgca agtccagtca gagccttta tatagtagca tcaaaagaa ctacttggcc           120 tggtaccagc agagaccagg gcagtctcct aaactgctga tttactgggc atccactggg          180
gaatctgggg tccctgatcg cttcacaggc agtggatctg gacagattt cactctcacc          240 atcagcagtg tgaaggctga agacctggca gtttattact gtcagcaata ttatagctat          300
ccgctcacgt tcggtgctgg gaccaagctg gagctgaaac gggctgatgc tgcaccaact          360
gtatccaaa                                                                  369
```